US00PP11091P

United States Patent [19]

Ballin

[11] Patent Number: Plant 11,091

[45] Date of Patent: Oct. 12, 1999

[54] HYBRID TEA ROSE PLANT NAMED 'BALPARTY'

[75] Inventor: Donald R. Ballin, 249 Barberry Rd., Highland Park, Ill. 60035

[73] Assignee: Donald R. Ballin, Highland Park, Ill.

[21] Appl. No.: 09/009,852

[22] Filed: Jan. 21, 1998

[51] Int. Cl.[6] ..... A01H 5/00

[52] U.S. Cl. ..... Plt./130

[58] Field of Search ..... Plt./130, 132, 133, Plt./134

[56] References Cited

U.S. PATENT DOCUMENTS

P.P. 1,814 3/1959 Swim ..... Plt./134

*Primary Examiner*—Howard J. Locker

[57] ABSTRACT

A new and distinct variety of hybrid tea rose plant named 'Balparty' is described and illustrated herein, said plant being a sport of 'Garden Party'. The new variety blooms continually and abundantly, with fully double exhibition quality blooms of excellent substance. The blooms exhibit a color range from white with pink edges to cream graduating to lemon yellow toward the center with pink suffusion at the petal edges, and the plant is characterized by a vigorous, upright, bushy growth habit and good disease resistance. The blooms exhibit a sweet fragrance.

4 Drawing Sheets

I discovered this sport of Garden Party, U.S. Plant Pat. No. 1,814, a hybrid tea rose, in my garden in 1992 as a single lateral growing on the parent plant. I budded several eyes on seedling multiflora understock and observed them for the next two years to be sure they differed sufficiently from Garden Party. I was convinced it was truly a sport. I sent a plant to several prominent rosarians in other areas of the country with the proviso they would not asexually reproduce this cultivar, give budwood to anyone or sell the plant. They concurred it was different than Garden Party.

It displays typical hybrid tea characteristics:

1) Produces one bloom per stem, sometimes with several side buds

2) Blooms continually and abundantly

3) Has fully double exhibition quality blooms of excellent substance

4) Exhibits a color range from white with pink edges to cream graduating to lemon yellow toward the center also with pink suffusion at the petal edges 5) Has a sweet fragrance 6) Has vigorous, upright, bushy growth habit 7) Has distinctive, reddish mahogany new growth 8) Appears to be well suited for the home garden 9) Has good disease resistance The present plant is distinguished from its parent by the following:

1. A greater petal count than Garden Party
2. A different and stronger fragrance
3. A unique color variation that will display flowers of white with pink edges and/or yellow with pink edges.
4. A greater disease resistance than Garden Party
5. A different flower form
6. A more compact plant, well suited for garden use
7. A highly distinctive reddish-purple color on new stems and foliage To date, there have been over 50 plants budded in my home garden and 6 successful cuttings, all growing true to the new variety. The name, 'Balparty' has been registered with the American Rose Society acting as the International Rose Registrar, with an exhibition and market name of 'Rose Odyssey 2000.'

Figure 1:
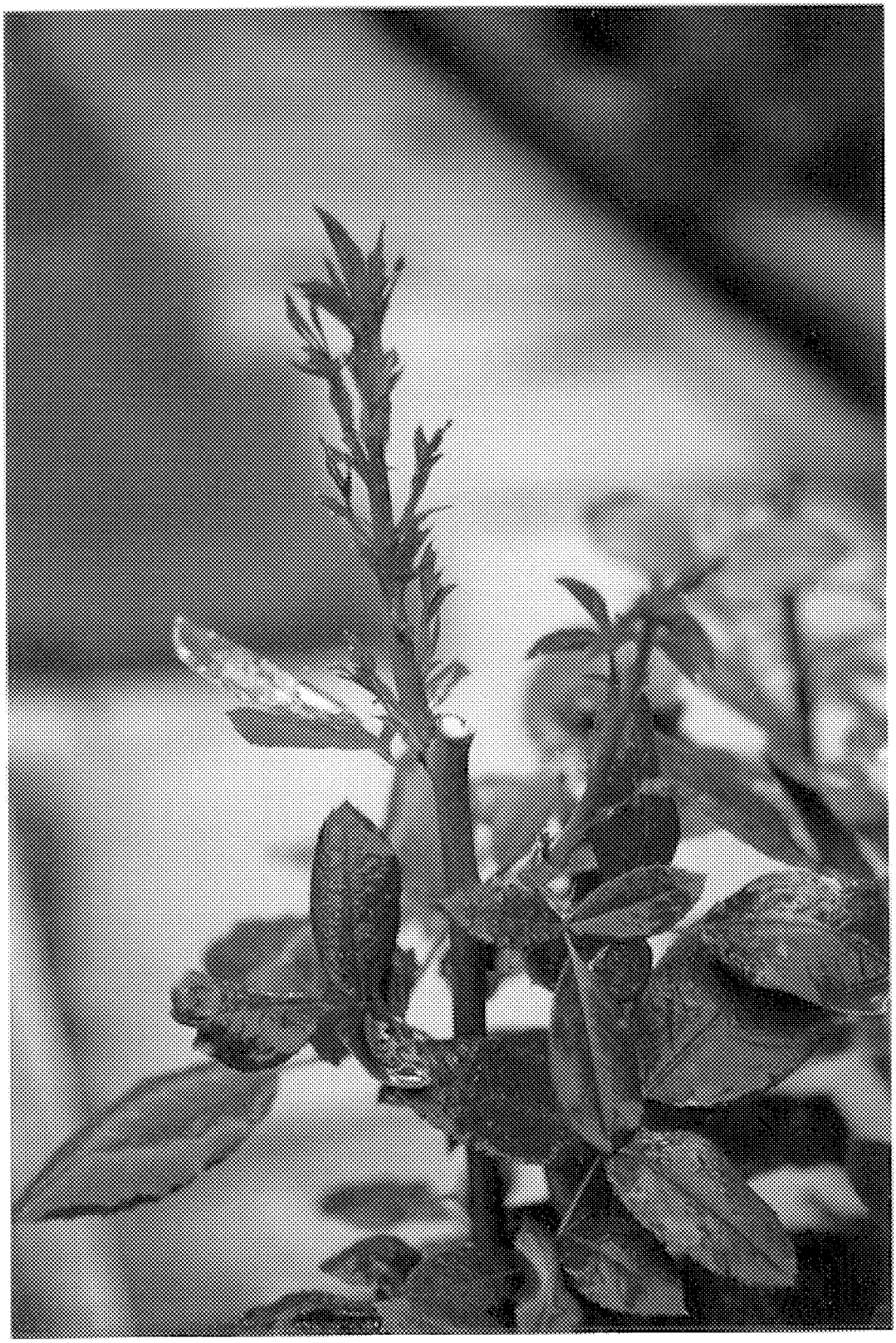
FIG. 1 shows vegetative growth, including new shoots, stems and foliage.
Figure 2:
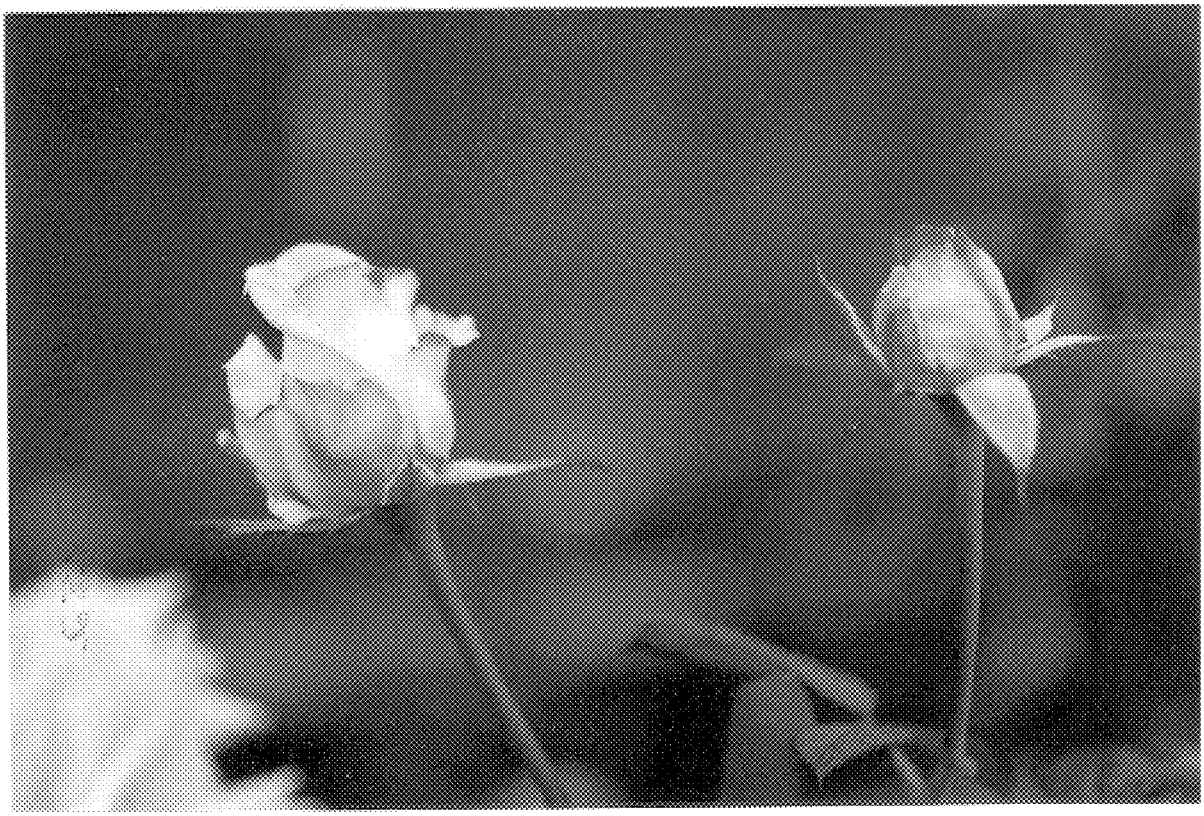
FIG. 2 shows a bud with sepals parting and a bud with sepals down and petals beginning to unfurl.
Figure 3:
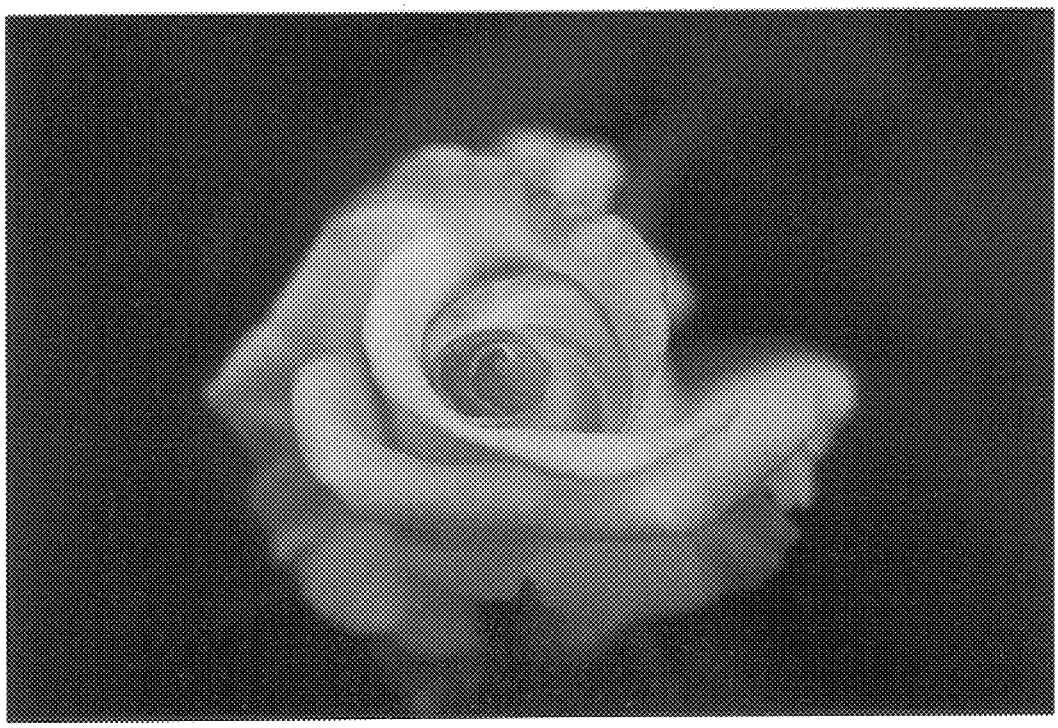
FIG. 3 shows a flower ⅓ to ½ open, coloration being representative of cool weather conditions.
Figure 4:
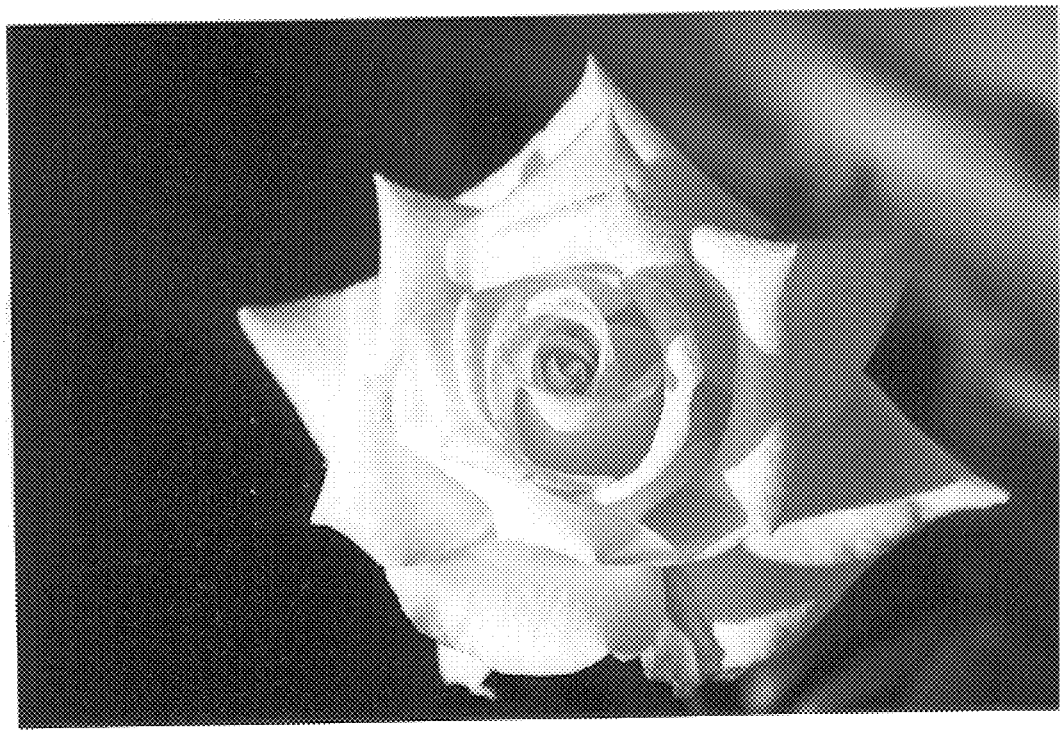
FIG. 4 shows a flower about ⅔ to ¾ open, coloration being representative of warm weather conditions.
Figure 5:
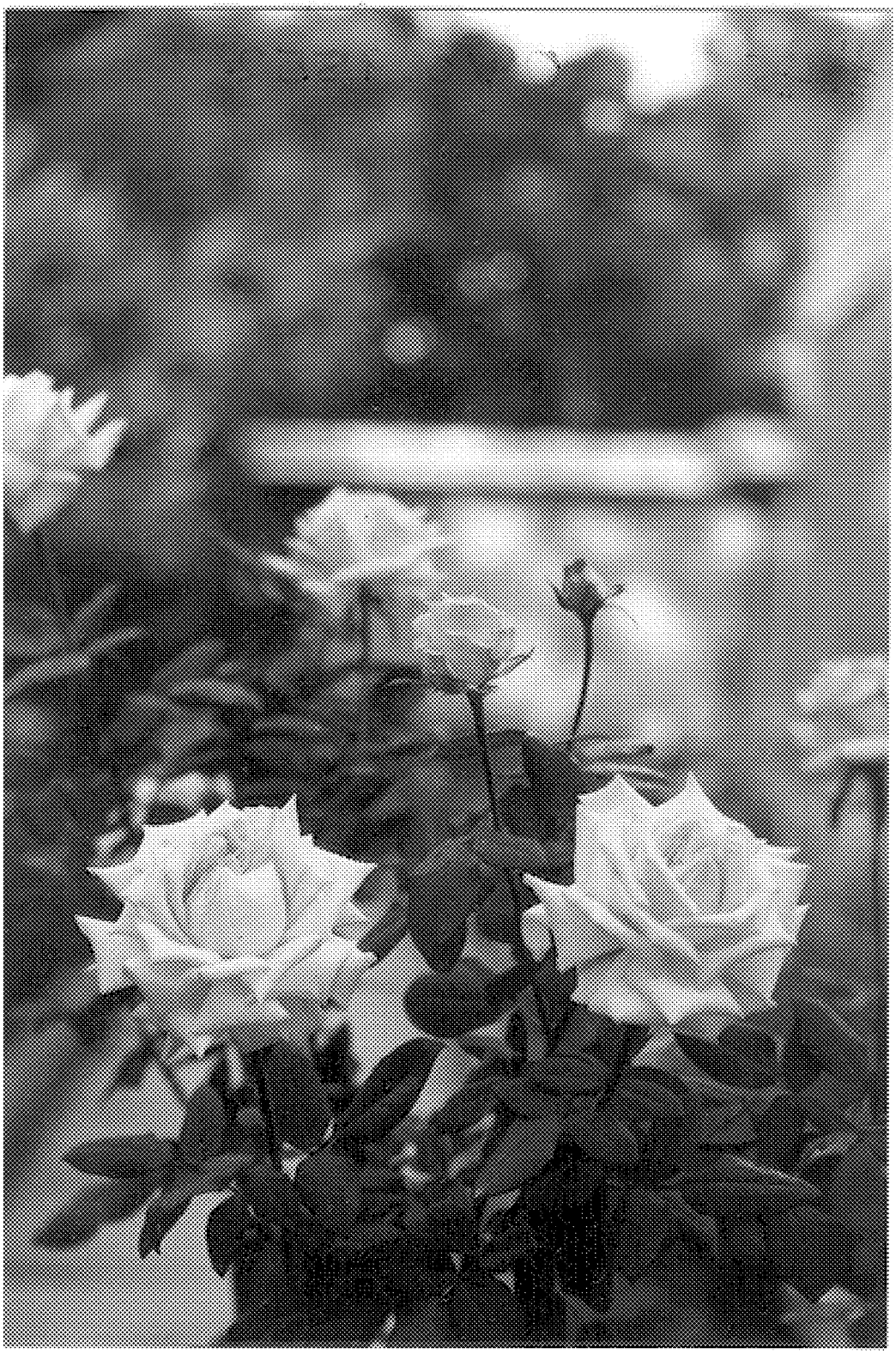
FIG. 5 illustrates typical vegetative growth as well as showing the bloom in varying stages of maturity.

The accompaying photographs of stems, foliage, buds, flowers and other anatomical parts are typical of this new variety. The flower photos in particular show the color variation that can occur due to the weather and location of the plant. In warmer weather the creamy tones can be observed more readily. In cooler weather the pink flush can be more pronounced. If the location of the plant is in an area of higher zinc concentrations, the pink flushing is greatly increased. The color in these photos is quite close to that which will appear in the garden.

The following descriptive run down of 'Balparty' uses color designations as found in the "R.H.S. Colour Chart" published by The Royal Horticultural Society of England, except where dictionary definition of color is applicable. The plants observed were one, two and three years old, budded on *Rosa multiflora* in my back yard at 249 Barberry Road, Highland Park, Ill. 60035 U.S.A.

'Balparty'

Parentage: Sport of "Garden Party" U.S. Plant Pat. No. 1,814.

Class: Hybrid Tea.

Height: 3½' to 4½' by end of growing season.

Habit: Upright; bushy.

Stem length: About 20" to 26" on average.

Inflorescence: Flowers per stem: generally one, sometimes three.

Bud (before parting of the sepals)

Size: ¾" to 1" in length.

Form: Ovoid, pointed.

Sepals:

*Color*—Yellow Green group 144 C.

*Surface texture.*—Outer Surface: Pubescent. Inner Surface: Covered with white fuzzy hairlike growth. There are generally two heavily appendaged or bearded sepals and three with smooth edges, but sometimes the reverse occurs with 3 appendaged and two with smooth edges appearing.

Peduncle:

*Length.*—Medium, 4½" to 6 ½".

*Surface.*—Pubescent. Color: Before bud opens, Yellow Green group 144 B; When flower is open, Green group 143 A.

*Strength.*—Rigid and erect.

Bud (after parting of the sepals)

Size: 1" to 2" in length.

Guard petals: Can be crumpled and deformed with variegated green striping but more often appear normal and sometimes have a single green stripe down the center of the petal.

Color: Reverse is blotched at edges and deep into the petal with color Red-Purple group varying from 61 B and C to 63 A and B to 67 A and B with random areas of White Group varying from 155 A to a shade lighter than 155 D and blending down toward the petal hinge in the Green Yellow group from 1 D to 1 B. The interior, i.e. upper side of the petal varies from Yellow group 2 D to 3 D to Green Yellow group 1 D blending down to the petal hinge from Green Yellow group 1 B to 1 A.

Flower (¼ to ¾ open): Petal edge is in the Red-Purple group and varies from 62 C on the upper side to 62 A on the reverse. Petal interior, upper side, outer 2 or 3 rows varies from Green White group 157 D to a shade or two whiter which is not recorded in these charts. The upper side of the interior rows of petals vary from Yellow group 2 D to Green Yellow group 1 D, deepening to 3 B at the petal hinge. (Full open to fading) Petal edge is in the Red Purple group varying from 68 C and D to 65 A and B to 70 D with color veining present on the inside of the petal. The petal interior is in the Green White group somewhat lighter than 157 D.

Fragrance: Moderate to strong, sweet, tending toward old garden rose fragrance.

Petalage: 32 to 44 and can have a varying number of petaloids.

Petal texture: Moderate to thick.

Form: High centered, with outer petals recurving to form star shapes when viewed from the top at the ½ to ¾ open stage.

Size: Medium to large, 4" to 5" when fully open.

Lasting quality: 5 to 8 days on the plant depending on weather. 5 to 6 days as a cut flower.

Reproductive parts:

*Anthers.*—Size: Medium. Quantity: Many. Color: Yellow. Arrangement: slightly irregular around styles.

*Filaments.*—Color: Yellow. Length: somewhat irregular.

*Stigmas.*—Color: pink.

*Styles.*—Color: reddish pink.

Foliage: Leaves, can have 3,5 or 7 leaflets.

*Leaflets.*—Shape: Oval to pointed oval. Edge Serration: usually small and regular but can be somewhat coarse and irregular. Texture: moderately leather. Appearance: semi-glossy. Color: new growth Usually appears to be in the Greyed Purple group, 187 A and B, with the reverse, i.e. underside, varying from Greyed Purple group 184 A and B to Greyed Orange group 176 A and B. Mature leaves can vary from Green group 137 A and B to 139 A with a lighter green reverse, Greyed Green Group 195 C.

*Petioles.*—Color: reddish on new growth becoming green on mature growth. Underside: has several curved prickles of varying sizes.

*Stipules.*—Adnate, pectinate, of medium width having short pointed auricles.

*Wood.*—Color: new growth usually appears to be in the Greyed Purple group 187 B and C. Mature stems usually vary from Green group 137 B to 137 D.

*Prickles.*—Quantity: numerous on basal canes, somewhat fewer on laterals with few to none on the upper third. Size: medium to large. Form: On basal canes can vary from the top surface having a slight downward curve and the under surface having a more pronounced curve, broadening at the base, to a slight downward curving top and a hump in the more pronounced curve of the under surface where it joins the stem. On lateral stems they are usually curved slightly downward. Color: usually varies from Greyed Red group 181 A to 178 A and B. These characteristics as observed in Highland Park, Ill. may vary somewhat in other parts of the world.

Disease resistance: More resistant to mildew then Garden Party.

I claim:

1. A new and distinct variety of Hybrid Tea Rose plant substantially as herein described and illustrated.

* * * * *